United States Patent
Schmale et al.

(10) Patent No.: US 9,370,315 B2
(45) Date of Patent: Jun. 21, 2016

(54) APPARATUS AND METHOD FOR INFLUENCING AND/OR DETECTING MAGNETIC PARTICLES COMPRISING BRIDGE UNIT

(71) Applicant: KONINKLIJKE PHILIPS N.V., Eindhoven (NL)

(72) Inventors: Ingo Schmale, Hamburg (DE); Bernhard Gleich, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/705,047

(22) Filed: May 6, 2015

(65) Prior Publication Data
US 2016/0081579 A1 Mar. 24, 2016

(30) Foreign Application Priority Data
May 14, 2014 (EP) .................................... 14168213

(51) Int. Cl.
G01V 3/00 (2006.01)
A61B 5/05 (2006.01)
G01R 33/10 (2006.01)

(52) U.S. Cl.
CPC .............. *A61B 5/0515* (2013.01); *G01R 33/10* (2013.01)

(58) Field of Classification Search
CPC ................................ G01R 33/10; A61B 5/0515
See application file for complete search history.

(56) References Cited

U.S. PATENT DOCUMENTS

2011/0241663 A1 10/2011 Gleich
2015/0276902 A1* 10/2015 Weaver .............. G01R 33/4808
324/309

FOREIGN PATENT DOCUMENTS

| WO | 2010070547 A1 | 6/2010 |
| WO | 2010134006 A2 | 11/2010 |
| WO | 2014071196 A1 | 5/2014 |
| WO | 2014147589 A1 | 9/2014 |

OTHER PUBLICATIONS

Graeser, Matthias et al., Analog Receive Signal Processing for Magnetic Particle Imaging, Medical Physics, vol. 40, No. 4, Apr. 2013.

* cited by examiner

*Primary Examiner* — Daniel Miller

(57) ABSTRACT

The present invention relates to an apparatus and a method for influencing and/or detecting magnetic particles in a field of view (28). The apparatus comprises selection means for generating a magnetic selection field (50) and drive and receiving means comprising one or more combined drive field and selection coils (441) for changing the position in space of the two sub-zones (52, 54) in the field of view (28) and for acquiring detection signals. A balanced bridge unit (160) comprising inductive or capacitive coupling elements (411, 421) is provided between the drive field signal generator unit (122) and the signal receiving unit (140) as a light-weight, inexpensive and easily implementable solution for reducing the harmonic background.

15 Claims, 10 Drawing Sheets

APPARATUS AND METHOD FOR INFLUENCING AND/OR DETECTING MAGNETIC PARTICLES COMPRISING BRIDGE UNIT

FIELD OF THE INVENTION

The present invention relates to an apparatus and a method for influencing and/or detecting magnetic particles in a field of view. Further, the present invention relates to a computer program for implementing said method on a computer and for controlling such an apparatus. The present invention relates particularly to the field of Magnetic Particle Imaging.

BACKGROUND OF THE INVENTION

Magnetic Particle Imaging (MPI) is an emerging medical imaging modality. The first versions of MPI were two-dimensional in that they produced two-dimensional images. Newer versions are three-dimensional (3D). A four-dimensional image of a non-static object can be created by combining a temporal sequence of 3D images to a movie, provided the object does not significantly change during the data acquisition for a single 3D image.

MPI is a reconstructive imaging method, like Computed Tomography (CT) or Magnetic Resonance Imaging (MRI). Accordingly, an MP image of an object's volume of interest is generated in two steps. The first step, referred to as data acquisition, is performed using an MPI scanner. The MPI scanner has means to generate a static magnetic gradient field, called the "selection field", which has a (single or more) field-free point(s) (FFP(s)) or a field-free line (FFL) at the isocenter of the scanner. Moreover, this FFP (or the FFL; mentioning "FFP" in the following shall generally be understood as meaning FFP or FFL) is surrounded by a first sub-zone with a low magnetic field strength, which is in turn surrounded by a second sub-zone with a higher magnetic field strength. In addition, the scanner has means to generate a time-dependent, spatially nearly homogeneous magnetic field. Actually, this field is obtained by superposing a rapidly changing field with a small amplitude, called the "drive field", and a slowly varying field with a large amplitude, called the "focus field". By adding the time-dependent drive and focus fields to the static selection field, the FFP may be moved along a predetermined FFP trajectory throughout a "volume of scanning" surrounding the isocenter. The scanner also has an arrangement of one or more, e.g. three, receive coils and can record any voltages induced in these coils. For the data acquisition, the object to be imaged is placed in the scanner such that the object's volume of interest is enclosed by the scanner's field of view, which is a subset of the volume of scanning.

The object must contain magnetic nanoparticles or other magnetic non-linear materials; if the object is an animal or a patient, a tracer containing such particles is administered to the animal or patient prior to the scan. During the data acquisition, the MPI scanner moves the FFP along a deliberately chosen trajectory that traces out/covers the volume of scanning, or at least the field of view. The magnetic nanoparticles within the object experience a changing magnetic field and respond by changing their magnetization. The changing magnetization of the nanoparticles induces a time-dependent voltage in each of the receive coils. This voltage is sampled in a receiver associated with the receive coil. The samples output by the receivers are recorded and constitute the acquired data. The parameters that control the details of the data acquisition make up the "scan protocol".

In the second step of the image generation, referred to as image reconstruction, the image is computed, or reconstructed, from the data acquired in the first step. The image is a discrete 3D array of data that represents a sampled approximation to the position-dependent concentration of the magnetic nanoparticles in the field of view. The reconstruction is generally performed by a computer, which executes a suitable computer program. Computer and computer program realize a reconstruction algorithm. The reconstruction algorithm is based on a mathematical model of the data acquisition. As with all reconstructive imaging methods, this model can be formulated as an integral operator that acts on the acquired data; the reconstruction algorithm tries to undo, to the extent possible, the action of the model.

Such an MPI apparatus and method have the advantage that they can be used to examine arbitrary examination objects—e. g. human bodies—in a non-destructive manner and with a high spatial resolution, both close to the surface and remote from the surface of the examination object. Such an apparatus and method are generally known and have been first described in DE 101 51 778 A1 and in Gleich, B. and Weizenecker, J. (2005), "Tomographic imaging using the nonlinear response of magnetic particles" in Nature, vol. 435, pp. 1214-1217, in which also the reconstruction principle is generally described. The apparatus and method for magnetic particle imaging (MPI) described in that publication take advantage of the non-linear magnetization curve of small magnetic particles.

MPI is based on the detection of harmonics as generated by magnetic (nano-) particles subjected to an external sinusoidal magnetic field excitation. Opposed to MR, excitation and reception are taking place simultaneously and are solely separated in the frequency domain. Conventionally, separation is realised by notch filters (LC resonators). Due to the higher sensitivity of coils that are nearest to the patient, there is a "competition" between drive (Tx-) and receive (Rx-) coil on the space very near around the patient. Further, within the magnetic field generator, various undesired signals limit the ultimate sensitivity of the set-up.

SUMMARY OF THE INVENTION

It is an object of the present invention to provide an apparatus and a method for influencing and/or detecting magnetic particles in a field of view that achieves harmonic background reduction without reducing the size of the field of view, in particular the bore size of a bore of the apparatus into which a patient can be placed. Further, a light-weight, inexpensive and easily implementable solution for reducing the "harmonic background", i.e. the "floor" of detected harmonics that is detected even when no nano-particles are inserted into the apparatus.

In a first aspect of the present invention an apparatus for influencing and/or detecting magnetic particles in a field of view is presented, which apparatus comprises:
  a selection field signal generator unit and selection field elements for generating a magnetic selection field having a pattern in space of its magnetic field strength such that a first sub-zone having a low magnetic field strength where the magnetization of the magnetic particles is not saturated and a second sub-zone having a higher magnetic field strength where the magnetization of the magnetic particles is saturated are formed in the field of view,
  a drive field signal generator unit, a signal receiving unit and a drive-receiving coil, said drive-receiving coil being configured both for changing the position in space of the two sub-zones in the field of view by means of a magnetic drive field so that the magnetization of the magnetic material changes locally and for acquiring detection signals, which detection signals depend on the magnetization in the field of view, which magnetization is influenced by the change in the position in space of the first and second sub-zone, a bridge unit coupled between said drive field signal generator unit and said signal receiving unit, said bridge unit comprising a first bridge sub-unit comprising a first inductive or capacitive coupling element, a second bridge sub-unit comprising a second inductive or capacitive coupling element, a third bridge sub-unit coupled in series with said first bridge sub-unit, said third bridge sub-unit comprising a measurement inductor, and a fourth bridge sub-unit coupled in series with said second bridge sub-unit, said fourth bridge sub-unit comprising said drive-receiving coil, and a coupling unit coupled between the drive field signal generator unit and the bridge unit for coupling into the bridge unit, wherein the signal receiving unit is coupled to a first output terminal arranged between the first and second bridge sub-units and a second output terminal arranged between the third and fourth bridge sub-units.

In a further aspect of the present invention a corresponding method is presented.

In yet a further aspect of the present invention a computer program is presented comprising program code means for causing a computer to control an apparatus as according to the present invention to carry out the steps of the method proposed according to the present invention when said computer program is carried out on the computer.

Preferred embodiments of the invention are defined in the dependent claims. It shall be understood that the claimed method and the claimed computer program have similar and/or identical preferred embodiments as the claimed apparatus and as defined in the dependent claims.

Since there is crosstalk from the transmit side to the receive side, precisely harmonics generated from the power amplifier, a lot of effort is spent on the band pass filter as conventionally used to ensure that no harmonics from the drive field enter the receive path. However, it was found, that the success of this effort is limited finally by the component of the filter itself: particularly capacitors (but also other components and materials) behave nonlinearly. The degree to which they are non-linear is so small that it is hard to measure and it seems to be of no concern to other applications. Nevertheless it becomes limiting for this reception scheme, despite efforts to identify an optimum capacitor technology.

One solution is to employ a gradiometer-based reception scheme, e.g. to have access to the fundamental frequency response of the magnetic particles. These gradiometer solutions are based on a dedicated receive coil, which receive the harmonic response from the magnetic particles (desired effect) but also the drive signal that excites these magnetic particles (undesired effect). To compensate the undesired drive signal, a second coil "balancing coil" is employed, which receives the same drive signal, but is connected with inverted polarity. For a bore-like drive-field generation, the dedicated receive coil is inside the transmit coils. Whilst this is beneficial with respect to signal strength (it has higher sensitivity being nearer to the magnetic particles), the strong disadvantage is that the bore size remaining for the patient (animal, object under investigation, . . . ) is reduced. The compensation coil needs to couple to the drive signal only.

This can be achieved in two ways: either it is also within or near to the drive field generating transmit coils, or it couples to another external inductor through which the same current flows as through the drive field coil.

According to the present invention suppression of harmonic background in the receive path is achieved by using a balanced bridge topology, but without the reduction of bore size of the apparatus for placement of the patient by inset coils. For this purpose a bridge unit comprising four bridge sub-units, one of which including a measurement inductor and another one of which including a drive-receiving coil, is used. Said drive-receiving coil represents a combined drive field and receiving coil (i.e. functions both as conventional drive field coil and as receiving coil). By symmetry, the balanced bridge topology cancels noise and harmonics emanating from the signal source (power amplifier and Tx band pass filter) at the input to the signal receiving unit, but requires limited efforts and costs to implement. The bridge unit and the drive field signal generator unit are coupled, in particular inductively or capacitively.

Generally, according to the proposed magnetic particle imaging apparatus and method the magnetic gradient field (i.e. the magnetic selection field) is generated with a spatial distribution of the magnetic field strength such that the field of view comprises a first sub-area with lower magnetic field strength (e.g. the FFP), the lower magnetic field strength being adapted such that the magnetization of the magnetic particles located in the first sub-area is not saturated, and a second sub-area with a higher magnetic field strength, the higher magnetic field strength being adapted such that the magnetization of the magnetic particles located in the second sub-area is saturated. Due to the non-linearity of the magnetization characteristic curve of the magnetic particles the magnetization and thereby the magnetic field generated by the magnetic particles shows higher harmonics, which, for example, can be detected by a detection coil. The evaluated signals (the higher harmonics of the signals) contain information about the spatial distribution of the magnetic particles, which again can be used e.g. for medical imaging, for the visualization of the spatial distribution of the magnetic particles and/or for other applications.

Thus, the apparatus and the method according to the present invention are based on a new physical principle (i.e. the principle referred to as MPI) that is different from other known conventional medical imaging techniques, as for example nuclear magnetic resonance (NMR). In particular, this new MPI-principle, does, in contrast to NMR, not exploit the influence of the material on the magnetic resonance characteristics of protons, but rather directly detects the magnetization of the magnetic material by exploiting the non-linearity of the magnetization characteristic curve. In particular, the MPI-technique exploits the higher harmonics of the generated magnetic signals which result from the non-linearity of the magnetization characteristic curve in the area where the magnetization changes from the non-saturated to the saturated state.

According to a preferred embodiment said coupling unit is configured for inductive coupling and comprises a primary coupling inductor, wherein said first bridge sub-unit comprises a first secondary coupling inductor and said second bridge sub-unit comprises a second secondary coupling inductor. Inductive coupling has the advantage that it provides for a galvanic separation avoiding unwanted ground loops. In an alternative embodiment said coupling unit is configured for capacitive coupling and comprises through-connections for connecting said drive field signal generator unit with a first input terminal arranged between the first and third bridge sub-units and a second input terminal arranged between the second and fourth bridge sub-units, wherein said first bridge sub-unit preferably comprises a capacitor and said second bridge sub-unit preferably comprises a capacitor.

In an advantageous embodiment, the coupling unit and/or the bridge unit are configured to obtain that U1/U2=Z1/Z2, wherein U1 is the voltage induced into the first inductive or capacitive coupling element, U2 is the voltage induced into the second inductive or capacitive coupling element, Z1 is the impedance of the series connection of the first and third bridge sub-units and Z2 is the impedance of the series connection of the second and fourth bridge sub-units. Preferably, the coupling unit and/or the bridge unit are configured to obtain that U1=U2 and Z1=Z2. Further preferably, the value of the first coupling element and/or the second coupling element are selected to obtain that U1/U2=Z1/Z2, in particular that U1=U2 and Z1=Z2. This provides that undesired harmonics and well as noise emanating from the signal source can be optimally suppressed.

In case of inductive coupling by the coupling unit, the coupling unit is preferably configured to mechanically change or set the coupling rate of the primary coupling inductor with the first and/or the second secondary coupling inductor. This can for instance be achieved by changing the location of the primary coupling inductor in one or more directions with respect to the first and/or the second secondary coupling inductor, e.g. by changing the distance of the primary coupling inductor with respect to the first and/or the second secondary coupling inductor. By changing or setting the coupling rate the degree of suppression of harmonics can be influenced.

Advantageously, said third and/or fourth bridge sub-unit comprises one or more bridge capacitors in series to said measurement inductor and said drive-receiving coil, respectively. Preferably, on each side of the measurement inductor and drive-receiving coil one or several capacitors are arranged in series to the measurement inductor and drive-receiving coil, respectively. The resonance frequency of the respective bride sub-unit can thus be controlled by setting the value of the bridge capacitors. Advantageously, the resonance frequency is set such as to be identical or nearly identical to the drive-field frequency (of the respective drive-field channel), thus yielding maximum current flow (and hence magnetic field strength) at minimum applied voltage.

In another embodiment said third bridge sub-unit comprises a third secondary coupling inductor coupled in series to said measurement inductor, said fourth bridge sub-unit comprises a fourth secondary coupling inductor coupled in series to said drive-receiving coil, and said coupling unit comprises a first coupling sub-unit for coupling with said first and second secondary coupling inductors and a second coupling sub-unit for coupling with said third and fourth secondary coupling inductors. In this way an even more symmetric coupling between the drive field signal generator unit and the bridge unit can be achieved.

Still further, in an embodiment the primary coupling inductor comprises two primary inductor elements for separately coupling to the first and second secondary coupling inductors, wherein said two primary inductor elements are coupled in series or in parallel. This allows to individually control the coupling to the secondary inductors and thus to influence the suppression of undesired harmonics and noise.

In still another embodiment the series connection of the first and third bridge sub-units and/or the series connection of the second and fourth bridge sub-units are configured to be in resonance with the drive field frequency of the magnetic drive field.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Before the details of the present invention shall be explained, basics of magnetic particle imaging shall be explained in detail with reference to FIGS. 1 to 4. In particular, four embodiments of an MPI scanner for medical diagnostics will be described. An informal description of the data acquisition will also be given. The similarities and differences between the different embodiments will be pointed out. Generally, the present invention can be used in all these different embodiments of an MPI apparatus.

Figure 1:
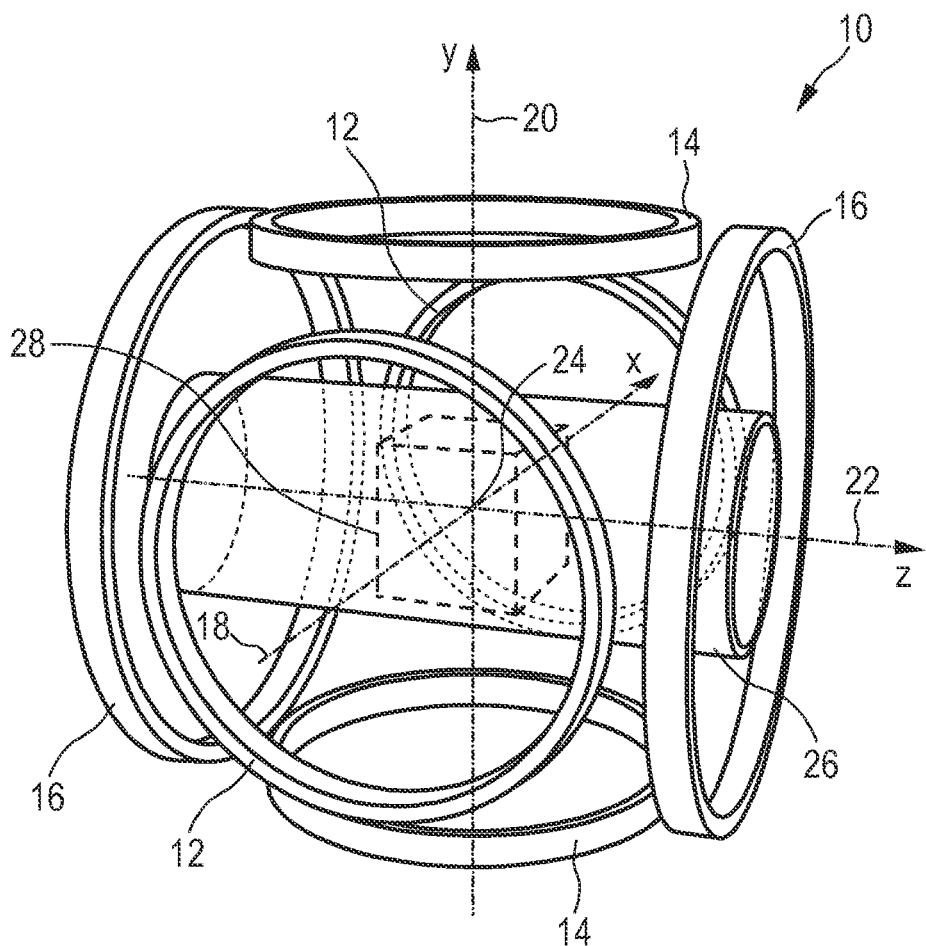
FIG. 1 shows a first embodiment of an MPI apparatus.

The first embodiment 10 of an MPI scanner shown in FIG. 1 has three pairs 12, 14, 16 of coaxial parallel circular coils, these coil pairs being arranged as illustrated in FIG. 1. These coil pairs 12, 14, 16 serve to generate the selection field as well as the drive and focus fields. The axes 18, 20, 22 of the three coil pairs 12, 14, 16 are mutually orthogonal and meet in a single point, designated the isocenter 24 of the MPI scanner 10. In addition, these axes 18, 20, 22 serve as the axes of a 3D Cartesian x-y-z coordinate system attached to the isocenter 24. The vertical axis 20 is nominated the y-axis, so that the x- and z-axes are horizontal. The coil pairs 12, 14, 16 are named after their axes. For example, the y-coil pair 14 is formed by the coils at the top and the bottom of the scanner. Moreover, the coil with the positive (negative) y-coordinate is called the $y^+$-coil ($y^-$-coil), and similarly for the remaining coils. When more convenient, the coordinate axes and the coils shall be labelled with $x_1$, $x_2$, and $x_3$, rather than with x, y, and z.

The scanner 10 can be set to direct a predetermined, time-dependent electric current through each of these coils 12, 14, 16, and in either direction. If the current flows clockwise around a coil when seen along this coil's axis, it will be taken as positive, otherwise as negative. To generate the static selection field, a constant positive current $I^S$ is made to flow through the $z^+$-coil, and the current $-I^S$ is made to flow through the $z^-$-coil. The z-coil pair 16 then acts as an anti-parallel circular coil pair.

It should be noted here that the arrangement of the axes and the nomenclature given to the axes in this embodiment is just an example and might also be different in other embodiments. For instance, in practical embodiments the vertical axis is often considered as the z-axis rather than the y-axis as in the present embodiment. This, however, does not generally change the function and operation of the device and the effect of the present invention.

Figure 2:
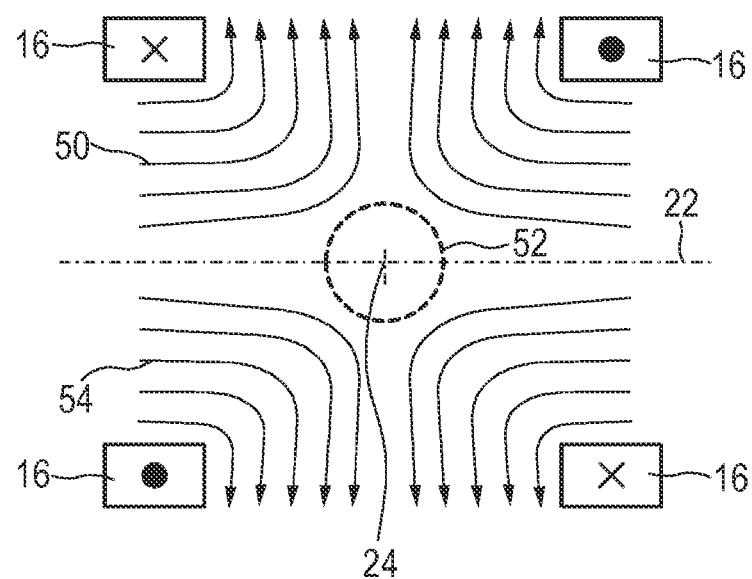
FIG. 2 shows an example of the selection field pattern produced by an apparatus as shown in FIG. 1.

The magnetic selection field, which is generally a magnetic gradient field, is represented in FIG. 2 by the field lines 50. It has a substantially constant gradient in the direction of the (e.g. horizontal) z-axis 22 of the z-coil pair 16 generating the selection field and reaches the value zero in the isocenter 24 on this axis 22. Starting from this field-free point (not individually shown in FIG. 2), the field strength of the magnetic selection field 50 increases in all three spatial directions as the distance increases from the field-free point. In a first sub-zone or region 52 which is denoted by a dashed line around the isocenter 24 the field strength is so small that the magnetization of particles present in that first sub-zone 52 is not saturated, whereas the magnetization of particles present in a second sub-zone 54 (outside the region 52) is in a state of saturation. In the second sub-zone 54 (i.e. in the residual part of the scanner's field of view 28 outside of the first sub-zone 52) the magnetic field strength of the selection field is sufficiently strong to keep the magnetic particles in a state of saturation.

By changing the position of the two sub-zones 52, 54 (including the field-free point) within the field of view 28 the (overall) magnetization in the field of view 28 changes. By determining the magnetization in the field of view 28 or physical parameters influenced by the magnetization, information about the spatial distribution of the magnetic particles in the field of view 28 can be obtained. In order to change the relative spatial position of the two sub-zones 52, 54 (including the field-free point) in the field of view 28, further magnetic fields, i.e. the magnetic drive field, and, if applicable, the magnetic focus field, are superposed to the selection field 50.

To generate the drive field, a time dependent current $I^D_1$ is made to flow through both x-coils 12, a time dependent current $I^D_2$ through both y-coils 14, and a time dependent current $I^D_3$ through both z-coils 16. Thus, each of the three coil pairs acts as a parallel circular coil pair. Similarly, to generate the focus field, a time dependent current $I^F_1$ is made to flow through both x-coils 12, a current $I^F_2$ through both y-coils 14, and a current $I^F_3$ through both z-coils 16.

It should be noted that the z-coil pair 16 is special: It generates not only its share of the drive and focus fields, but also the selection field (of course, in other embodiments, separate coils may be provided). The current flowing through the $z^+$-coil is $I^D_3+I^F_3\pm I^S$. The current flowing through the remaining two coil pairs 12, 14 is $I^D_k+I^F_k$, k=1, 2. Because of their geometry and symmetry, the three coil pairs 12, 14, 16 are well decoupled. This is wanted.

Being generated by an anti-parallel circular coil pair, the selection field is rotationally symmetric about the z-axis, and its z-component is nearly linear in z and independent of x and y in a sizeable volume around the isocenter 24. In particular, the selection field has a single field-free point (FFP) at the isocenter. In contrast, the contributions to the drive and focus fields, which are generated by parallel circular coil pairs, are spatially nearly homogeneous in a sizeable volume around the isocenter 24 and parallel to the axis of the respective coil pair. The drive and focus fields jointly generated by all three parallel circular coil pairs are spatially nearly homogeneous and can be given any direction and strength, up to some maximum strength. The drive and focus fields are also time-dependent. The difference between the focus field and the drive field is that the focus field varies slowly in time and may have a large amplitude, while the drive field varies rapidly and has a small amplitude. There are physical and biomedical reasons to treat these fields differently. A rapidly varying field with a large amplitude would be difficult to generate and potentially hazardous to a patient.

In a practical embodiment the FFP can be considered as a mathematical point, at which the magnetic field is assumed to be zero. The magnetic field strength increases with increasing distance from the FFP, wherein the increase rate might be different for different directions (depending e.g. on the particular layout of the device). As long as the magnetic field strength is below the field strength required for bringing magnetic particles into the state of saturation, the particle actively contributes to the signal generation of the signal measured by the device; otherwise, the particles are saturated and do not generate any signal.

The embodiment 10 of the MPI scanner has at least one further pair, preferably three further pairs, of parallel circular coils, again oriented along the x-, y-, and z-axes. These coil pairs, which are not shown in FIG. 1, serve as receive coils. As with the coil pairs 12, 14, 16 for the drive and focus fields, the magnetic field generated by a constant current flowing through one of these receive coil pairs is spatially nearly homogeneous within the field of view and parallel to the axis of the respective coil pair. The receive coils are supposed to be well decoupled. The time-dependent voltage induced in a receive coil is amplified and sampled by a receiver attached to this coil. More precisely, to cope with the enormous dynamic range of this signal, the receiver samples the difference between the received signal and a reference signal. The transfer function of the receiver is non-zero from zero Hertz ("DC") up to the frequency where the expected signal level drops below the noise level. Alternatively, the MPI scanner has no dedicated receive coils. Instead the drive field transmit coils are used as receive coils as is the case according to the present invention using combined drive-receiving coils.

The embodiment 10 of the MPI scanner shown in FIG. 1 has a cylindrical bore 26 along the z-axis 22, i.e. along the axis of the selection field. All coils are placed outside this bore 26. For the data acquisition, the patient (or object) to be imaged is placed in the bore 26 such that the patient's volume of interest—that volume of the patient (or object) that shall be imaged—is enclosed by the scanner's field of view 28—that volume of the scanner whose contents the scanner can image. The patient (or object) is, for instance, placed on a patient table. The field of view 28 is a geometrically simple, isocentric volume in the interior of the bore 26, such as a cube, a ball, a cylinder or an arbitrary shape. A cubical field of view 28 is illustrated in FIG. 1.

The size of the first sub-zone 52 is dependent on the strength of the gradient of the magnetic selection field and on the field strength of the magnetic field required for saturation, which in turn depends on the magnetic particles. For a sufficient saturation of typical magnetic particles at a magnetic field strength of 80 A/m and a gradient (in a given space direction) of the field strength of the magnetic selection field amounting to $50\times10^3$ A/m$^2$, the first sub-zone 52 in which the magnetization of the particles is not saturated has dimensions of about 1 mm (in the given space direction).

The patient's volume of interest is supposed to contain magnetic nanoparticles. Prior to the diagnostic imaging of, for example, a tumor, the magnetic particles are brought to the volume of interest, e.g. by means of a liquid comprising the magnetic particles which is injected into the body of the patient (object) or otherwise administered, e.g. orally, to the patient.

Generally, various ways for bringing the magnetic particles into the field of view exist. In particular, in case of a patient into whose body the magnetic particles are to be introduced, the magnetic particles can be administered by use of surgical and non-surgical methods, and there are both methods which require an expert (like a medical practitioner) and methods which do not require an expert, e.g. can be carried out by laypersons or persons of ordinary skill or the patient himself/herself. Among the surgical methods there are potentially non-risky and/or safe routine interventions, e.g. involving an invasive step like an injection of a tracer into a blood vessel (if such an injection is at all to be considered as a surgical method), i.e. interventions which do not require considerable professional medical expertise to be carried out and which do not involve serious health risks. Further, non-surgical methods like swallowing or inhalation can be applied.

Generally, the magnetic particles are pre-delivered or pre-administered before the actual steps of data acquisition are carried out. In embodiments, it is, however, also possible that further magnetic particles are delivered/administered into the field of view.

An embodiment of magnetic particles comprises, for example, a spherical substrate, for example, of glass which is provided with a soft-magnetic layer which has a thickness of, for example, 5 nm and consists, for example, of an iron-nickel alloy (for example, Permalloy). This layer may be covered, for example, by means of a coating layer which protects the particle against chemically and/or physically aggressive environments, e.g. acids. The magnetic field strength of the magnetic selection field 50 required for the saturation of the magnetization of such particles is dependent on various parameters, e.g. the diameter of the particles, the used magnetic material for the magnetic layer and other parameters.

In the case of e.g. a diameter of 10 µm with such magnetic particles, a magnetic field of approximately 800 A/m (corresponding approximately to a flux density of 1 mT) is then required, whereas in the case of a diameter of 100 µm a magnetic field of 80 A/m suffices. Even smaller values are obtained when a coating of a material having a lower saturation magnetization is chosen or when the thickness of the layer is reduced.

In practice, magnetic particles commercially available under the trade name Resovist (or similar magnetic particles) are often used, which have a core of magnetic material or are formed as a massive sphere and which have a diameter in the range of nanometers, e.g. 40 or 60 nm.

For further details of the generally usable magnetic particles and particle compositions, the corresponding parts of EP 1224542, WO 2004/091386, WO 2004/091390, WO 2004/091394, WO 2004/091395, WO 2004/091396, WO 2004/091397, WO 2004/091398, WO 2004/091408 are herewith referred to, which are herein incorporated by reference. In these documents more details of the MPI method in general can be found as well.

During the data acquisition, the x-, y-, and z-coil pairs 12, 14, 16 generate a position- and time-dependent magnetic field, the applied field. This is achieved by directing suitable currents through the field generating coils. In effect, the drive and focus fields push the selection field around such that the FFP moves along a preselected FFP trajectory that traces out the volume of scanning—a superset of the field of view. The applied field orientates the magnetic nanoparticles in the patient. As the applied field changes, the resulting magnetization changes too, though it responds nonlinearly to the applied field. The sum of the changing applied field and the changing magnetization induces a time-dependent voltage $V_k$ across the terminals of the receive coil pair along the $x_k$-axis. The associated receiver converts this voltage to a signal $S_k$, which it processes further.

Figure 3:
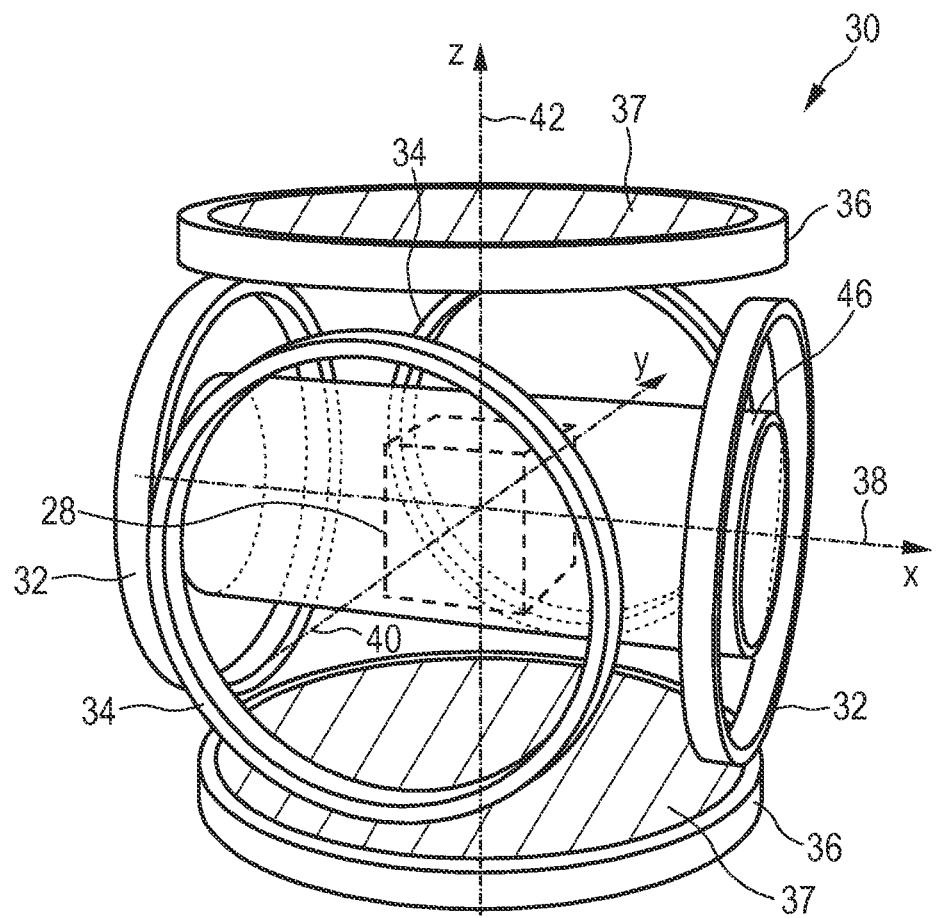
FIG. 3 shows a second embodiment of an MPI apparatus.

Like the first embodiment 10 shown in FIG. 1, the second embodiment 30 of the MPI scanner shown in FIG. 3 has three circular and mutually orthogonal coil pairs 32, 34, 36, but these coil pairs 32, 34, 36 generate the selection field and the focus field only. The z-coils 36, which again generate the selection field, are filled with ferromagnetic material 37. The z-axis 42 of this embodiment 30 is oriented vertically, while the x- and y-axes 38, 40 are oriented horizontally. The bore 46 of the scanner is parallel to the x-axis 38 and, thus, perpendicular to the axis 42 of the selection field. The drive field is generated by a solenoid (not shown) along the x-axis 38 and by pairs of saddle coils (not shown) along the two remaining axes 40, 42. These coils are wound around a tube which forms the bore. The drive field coils also serve as receive coils.

To give a few typical parameters of such an embodiment: The z-gradient of the selection field, G, has a strength of $G/\mu_0=2.5$ T/m, where $\mu_0$ is the vacuum permeability. The temporal frequency spectrum of the drive field is concentrated in a narrow band around 25 kHz (up to approximately 250 kHz). The useful frequency spectrum of the received signals lies between 50 kHz and 1 MHz (eventually up to approximately 15 MHz). The bore has a diameter of 120 mm. The biggest cube 28 that fits into the bore 46 has an edge length of $120$ mm$/\sqrt{2}\approx 84$ mm.

Since the construction of field generating coils is generally known in the art, e.g. from the field of magnetic resonance imaging, this subject need not be further elaborated herein.

In an alternative embodiment for the generation of the selection field, permanent magnets (not shown) can be used. In the space between two poles of such (opposing) permanent magnets (not shown) there is formed a magnetic field which is similar to that shown in FIG. 2, that is, when the opposing poles have the same polarity. In another alternative embodiment, the selection field can be generated by a mixture of at least one permanent magnet and at least one coil.

Figure 4A:
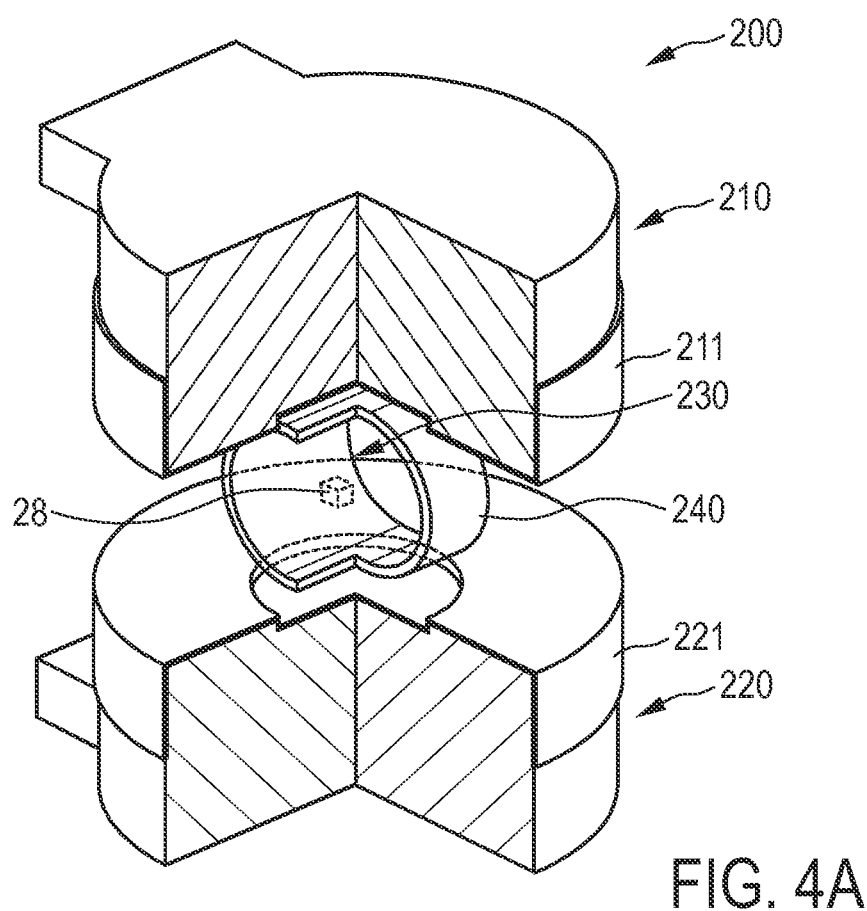
FIGS. 4A and 4B show a third and a fourth embodiment of an MPI apparatus, respectively.
Figure 4B:
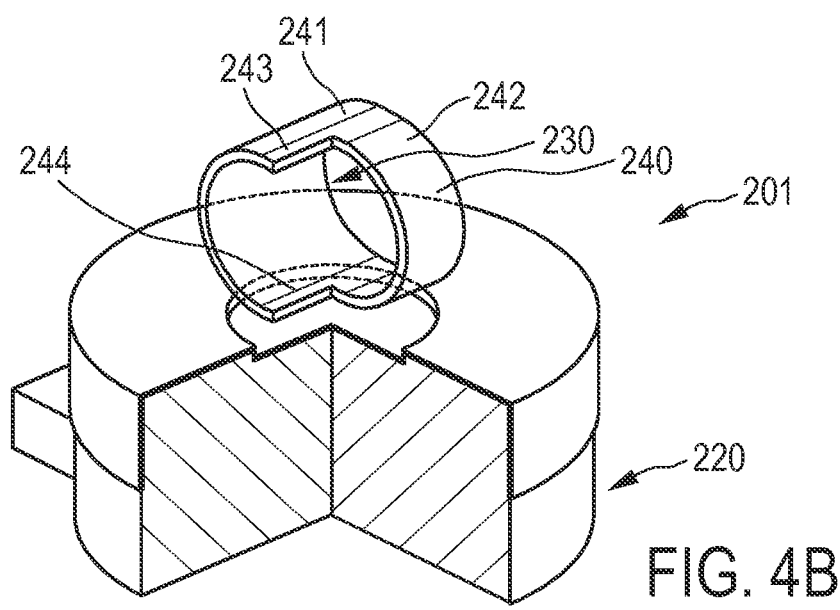

FIGS. 4A and 4B show two embodiments of the general outer layout of an MPI apparatus 200, 300. FIG. 4A shows an embodiment of the proposed MPI apparatus 200 comprising two selection-and-focus field coil units 210, 220 which are basically identical and arranged on opposite sides of the examination area 230 formed between them. Further, a drive field coil unit 240 is arranged between the selection-and-focus field coil units 210, 220, which are placed around the area of interest of the patient (not shown). The selection-and-focus field coil units 210, 220 comprise several selection-and-focus field coils for generating a combined magnetic field representing the above-explained magnetic selection field and magnetic focus field. In particular, each selection-and-focus field coil unit 210, 220 comprises a, preferably identical, set of selection-and-focus field coils. Details of said selection-and-focus field coils will be explained below.

The drive field coil unit 240 comprises a number of drive field coils for generating a magnetic drive field. These drive field coils may comprise several pairs of drive field coils, in particular one pair of drive field coils for generating a magnetic field in each of the three directions in space. In an embodiment the drive field coil unit 240 comprises two pairs of saddle coils for two different directions in space and one solenoid coil for generating a magnetic field in the longitudinal axis of the patient.

The selection-and-focus field coil units 210, 220 are generally mounted to a holding unit (not shown) or the wall of room. Preferably, in case the selection-and-focus field coil units 210, 220 comprise pole shoes for carrying the respective coils, the holding unit does not only mechanically hold the selection-and-focus field coil unit 210, 220 but also provides a path for the magnetic flux that connects the pole shoes of the two selection-and-focus field coil units 210, 220.

As shown in FIG. 4A, the two selection-and-focus field coil units 210, 220 each include a shielding layer 211, 221 for shielding the selection-and-focus field coils from magnetic fields generated by the drive field coils of the drive field coil unit 240.

In the embodiment of the MPI apparatus 201 shown in FIG. 4B only a single selection-and-focus field coil unit 220 is provided as well as the drive field coil unit 240. Generally, a single selection-and-focus field coil unit is sufficient for generating the required combined magnetic selection and focus field. Said single selection-and-focus field coil unit 220 may thus be integrated into a (not shown) patient table on which a patient is placed for the examination. Preferably, the drive field coils of the drive field coil unit 240 may be arranged around the patient's body already in advance, e.g. as flexible coil elements. In another implementation, the drive field coil unit 240 can be opened, e.g. separable into two subunits 241, 242 as indicated by the separation lines 243, 244 shown in FIG. 4B in axial direction, so that the patient can be placed in between and the drive field coil subunits 241, 242 can then be coupled together.

In still further embodiments of the MPI apparatus, even more selection-and-focus field coil units may be provided which are preferably arranged according to a uniform distribution around the examination area 230. However, the more selection-and-focus field coil units are used, the more will the accessibility of the examination area for placing a patient therein and for accessing the patient itself during an examination by medical assistance or doctors be limited.

Figure 5:
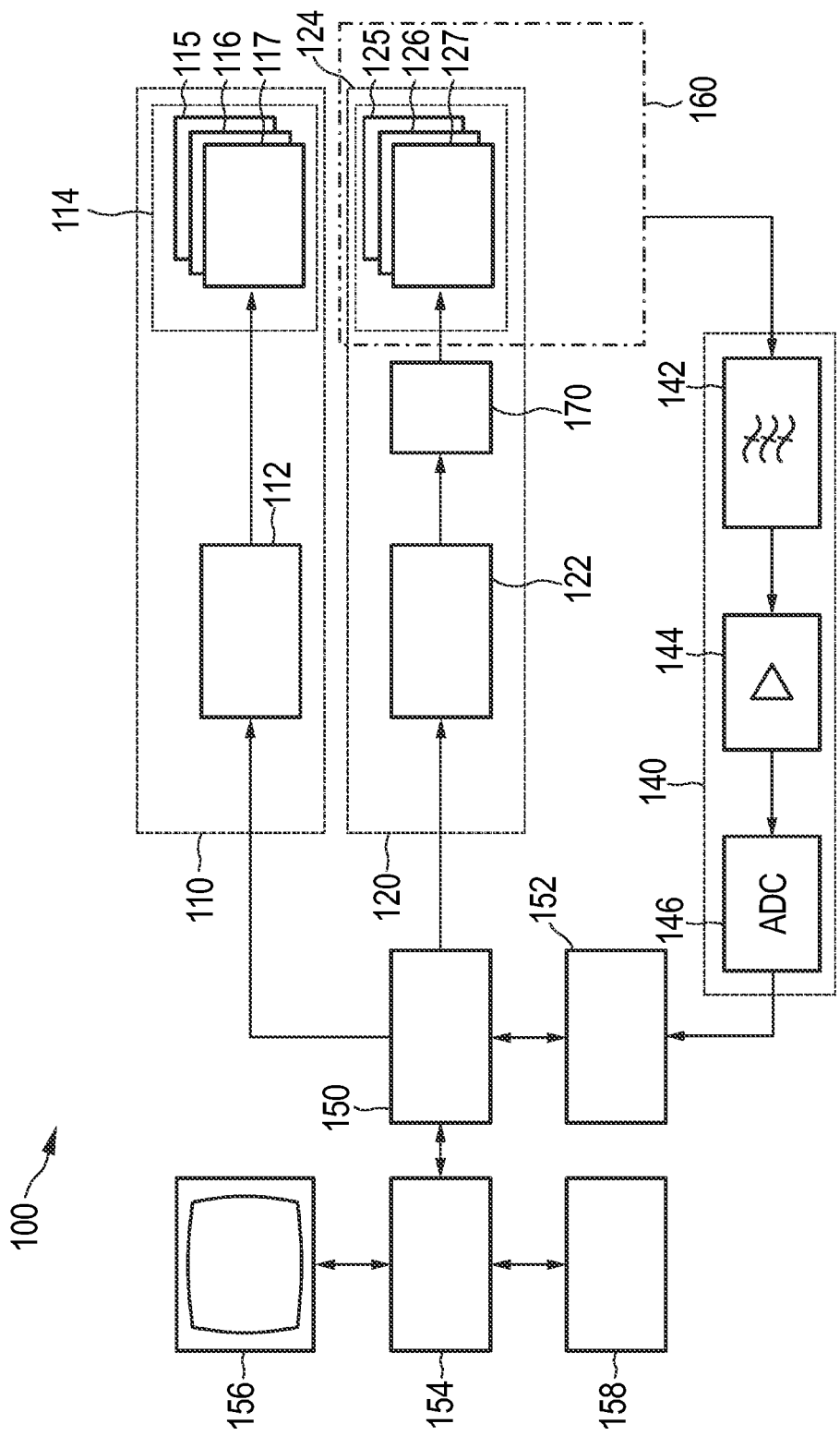
FIG. 5 shows a block diagram of an MPI apparatus according to the present invention.

FIG. 5 shows a general block diagram of an MPI apparatus 100 according to the present invention. The general principles of magnetic particle imaging explained above are valid and applicable to this embodiment as well, unless otherwise specified. The embodiment of the apparatus 100 shown in FIG. 5 comprises various coils for generating the desired magnetic fields. First, the coils and their functions in MPI shall be explained.

For generating the combined magnetic selection-and-focus field, selection-and-focus means 110 are provided. The magnetic selection-and-focus field has a pattern in space of its magnetic field strength such that the first sub-zone (52 in FIG. 2) having a low magnetic field strength where the magnetization of the magnetic particles is not saturated and a second sub-zone (54 in FIG. 2) having a higher magnetic field strength where the magnetization of the magnetic particles is saturated are formed in the field of view 28, which is a small part of the examination area 230, which is conventionally achieved by use of the magnetic selection field. Further, by use of the magnetic selection-and-focus field the position in space of the field of view 28 within the examination area 230 can be changed, as conventionally done by use of the magnetic focus field.

The selection-and-focus means 110 comprises at least one set of selection-and-focus field coils 114 and a selection-and-focus field generator unit 112 for generating selection-and-focus field currents to be provided to said at least one set of selection-and-focus field coils 114 (representing one of the selection-and-focus field coil units 210, 220 shown in FIGS. 4A, 4B) for controlling the generation of said magnetic selection-and-focus field. Preferably, a separate generator subunit is provided for each coil element (or each pair of coil elements) of the at least one set of selection-and-focus field coils 114. Said selection-and-focus field generator unit 112 comprises a controllable current source (generally including an amplifier) and a filter unit which provide the respective coil element with the field current to individually set the gradient strength and field strength of the contribution of each coil to the magnetic selection-and-focus field. It shall be noted that the filter unit 114 can also be omitted. Further, separate focus and selection means are provided in other embodiments.

For generating the magnetic drive field the apparatus 100 further comprises drive means 120 comprising a drive field signal generator unit 122 and a set of drive field coils 124 (representing the drive coil unit 240 shown in FIGS. 4A, 4B) for changing the position in space and/or size of the two sub-zones in the field of view by means of a magnetic drive field so that the magnetization of the magnetic material changes locally. As mentioned above said drive field coils 124 preferably comprise two pairs 125, 126 of oppositely arranged saddle coils and one solenoid coil 127. Other implementations, e.g. three pairs of coil elements, are also possible.

The drive field signal generator unit 122 preferably comprises a separate drive field signal generation subunit for each coil element (or at least each pair of coil elements) of said set of drive field coils 124. Said drive field signal generator unit 122 preferably comprises a drive field current source (preferably including a power amplifier) and a filter unit for providing a time-dependent drive field current to the respective drive field coil.

The selection-and-focus field signal generator unit 112 and the drive field signal generator unit 122 are preferably controlled by a control unit 150, which preferably controls the selection-and-focus field signal generator unit 112 such that the sum of the field strengths and the sum of the gradient strengths of all spatial points of the selection field is set at a predefined level. For this purpose the control unit 150 can also be provided with control instructions by a user according to the desired application of the MPI apparatus, which, however, is preferably omitted according to the present invention.

For using the MPI apparatus 100 for determining the spatial distribution of the magnetic particles in the examination area (or a region of interest in the examination area), particularly to obtain images of said region of interest, signal detection receiving means, in particular a receiving coil, and a signal receiving unit 140, which receives signals detected by said receiving means, are provided. Conventionally, one to three separate receiving coils are provided in an MPI apparatus as receiving means. According to the present invention, however, one to three of said drive field coils 124 (or drive field coil pairs) act (simultaneously or alternately) as receiving coils for receiving detection signals. Accordingly, these drive field coils are called "drive-receiving coils" herein.

The generation of magnetic drive fields and the detection of detection signals can be performed simultaneously or alternately. Preferably, all three drive-receiving coils (or coil pairs) 125, 126, 127 act as receiving coils and three receiving units 140—one per drive-receiving coil (or coil pair)—are provided in practice, but more than three drive-receiving coils and receiving units can be also used, in which case the acquired detection signals are not 3-dimensional but K-dimensional, with K being the number of drive-receiving coils.

Said signal receiving unit 140 comprises a filter unit 142 (also called Rx filter) for filtering the received detection signals. The aim of this filtering is to separate measured values, which are caused by the magnetization in the examination area which is influenced by the change in position of the two part-regions (52, 54), from other, interfering signals (in particular crosstalk of the fundamental frequency). To this end, the filter unit 142 may be designed for example such that signals which have temporal frequencies that are smaller than the temporal frequencies with which the drive-receiving coil(s) is (are) operated, or smaller than twice these temporal frequencies, do not pass the filter unit 142. The signals are then transmitted via an amplifier unit 144 (also called LNA, Low-Noise-Amplifier) to an analog/digital converter 146 (ADC).

The digitized signals produced by the analog/digital converter 146 are fed to an image processing unit (also called reconstruction means) 152, which reconstructs the spatial distribution of the magnetic particles from these signals and the respective position which the first part-region 52 of the first magnetic field in the examination area assumed during receipt of the respective signal and which the image processing unit 152 obtains from the control unit 150. The reconstructed spatial distribution of the magnetic particles is finally transmitted via the control means 150 to a computer 154, which displays it on a monitor 156. Thus, an image can be displayed showing the distribution of magnetic particles in the field of view of the examination area.

In other applications of the MPI apparatus 100, e.g. for influencing the magnetic particles (for instance for a hyperthermia treatment) or for moving the magnetic particles (e.g. attached to a catheter for moving the catheter or attached to a medicament for moving the medicament to a certain location) the receiving means may also be omitted or simply not used.

Further, an input unit 158 may optionally be provided, for example a keyboard. A user may therefore be able to set the desired direction of the highest resolution and in turn receives the respective image of the region of action on the monitor 156. If the critical direction, in which the highest resolution is needed, deviates from the direction set first by the user, the user can still vary the direction manually in order to produce a further image with an improved imaging resolution. This resolution improvement process can also be operated automatically by the control unit 150 and the computer 154. The control unit 150 in this embodiment sets the gradient field in a first direction which is automatically estimated or set as start value by the user. The direction of the gradient field is then varied stepwise until the resolution of the thereby received images, which are compared by the computer 154, is maximal, respectively not improved anymore. The most critical direction can therefore be found respectively adapted automatically in order to receive the highest possible resolution.

Still further, according to the present invention a bridge unit 160 is provided that is coupled between said drive field signal generator unit 122 and said signal receiving unit 140. Said bridge unit 160 comprises four bridge sub-units as will be explained in more detail below, wherein said drive-receiving coil 124 is part of one of said bridge sub-units. Still further, a coupling unit 170 is coupled between the drive field signal generator unit 122 and the bridge unit 160 for coupling into the bridge unit 160.

Figure 6:
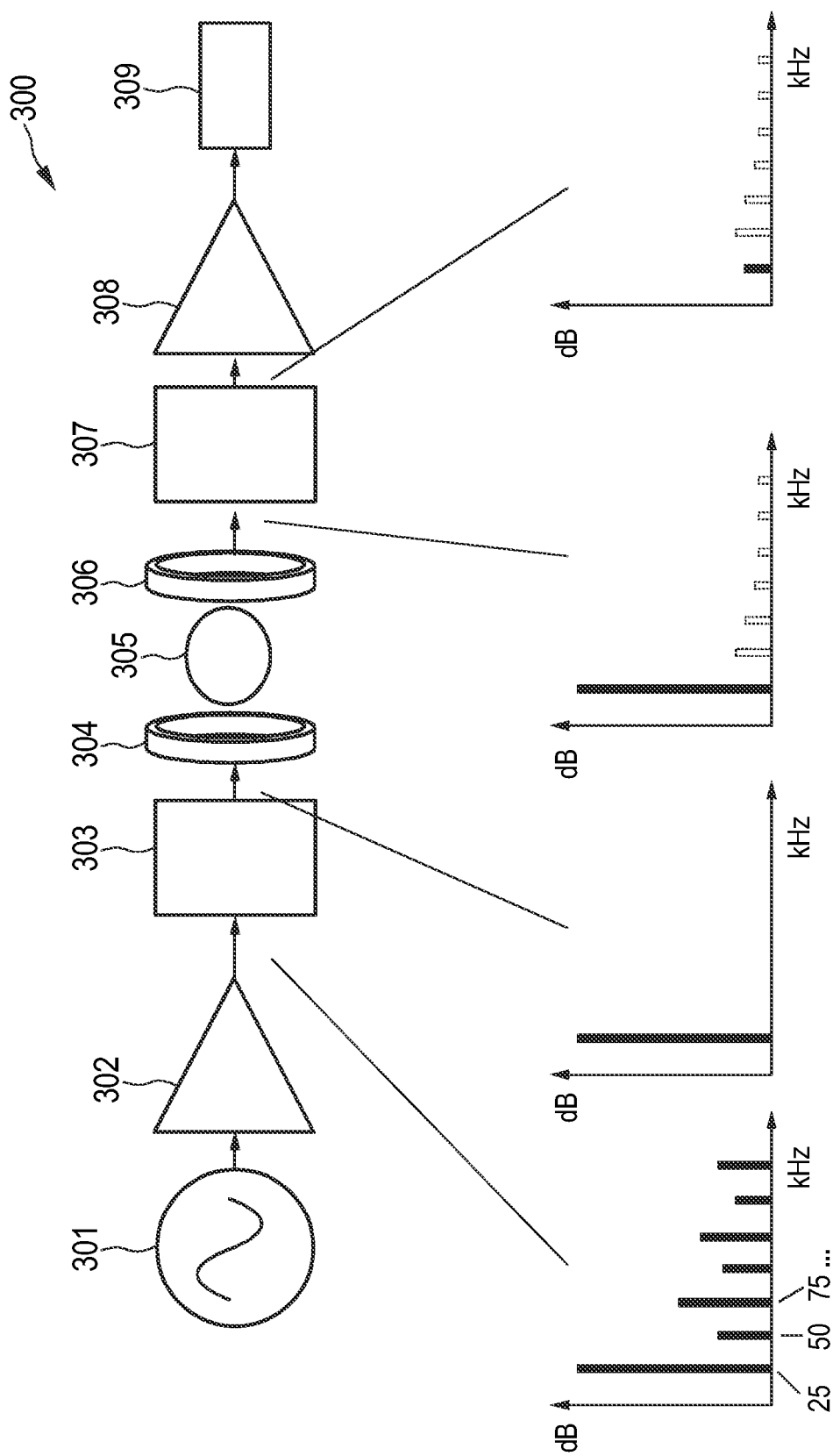
FIG. 6 shows a block diagram of the general filtering scheme as used in an MPI apparatus.

FIG. 6 shows a block diagram of the general filtering scheme 300 as used in an MPI apparatus and spectra of various signals taken at different connections in said filtering scheme. As explained above MPI is based on the detection of harmonics as generated by magnetic particles subjected to an external sinusoidal magnetic field excitation by use of a synthesizer 301 and a power amplifier 302, which (together with the band pass filter 303) basically represent the drive field signal generator unit 122 shown in FIG. 5. Excitation and reception (by use of a low-noise amplifier 308 and an ADC 309, which (together with the band stop filter 307) basically represent the signal receiving unit 140 shown in FIG. 5, are taking place simultaneously, and are solely separated in the frequency domain. The classic separation is realized by notch filters (e.g. LC resonators), i.e. a band pass filter 303 in front of the transmit coil 304 (drive field coil) and a band stop filter 307 after the receive coil 306, wherein said transmit coil 304 and said receive coil 306 are separate coils arranged close to the bore 305 in which the patient is placed for examination. Due to the higher sensitivity of coils that are nearest to the patient, there is a competition between the transmit coil 304 and the receive coil 306 on the space very near around the patient. This "competition" is solved according to the present invention by using a joint transmit/receive coil, i.e. a drive-receiving coil as mentioned above.

Since there is crosstalk from the transmit side to the receive side, in particular harmonics generated from the power amplifier 302, a lot of effort is spent on the band pass filter 303 to ensure that no harmonics from the drive field enter the receive path. However, it was found, that the success of this effort is limited finally by the component of the filter 303 itself: particularly the capacitors (but also other components and materials) behave non-linearily. The degree to which they are non-linear is so small that it is hard to measure and it seems to be of no concern to other applications. Nevertheless it becomes limiting for this reception scheme, despite efforts to identify an optimum capacitor technology.

The sensitivity of an MPI apparatus is generally limited by:
i. Noise, chiefly thermal noise, which is broad-band and emanates from lossy components. Low loss components or cooling help to minimize this.
ii. External interferers, which typically have a pronounced energy at distinctive frequencies. Such disturbing needles in the spectrum can emanate e.g. from long-wave radio broadcast operating in the MPI reception frequency range. A shielded cabinet is typically employed to minimize this.
iii. Harmonic background, i.e. harmonics that appear without any nanoparticles being present. Various sources of harmonics exist.
   a) Nonlinearity of the DF power amplifier. To stop this, the Tx band pass filter is implemented.
   b) Nonlinearity of the filtering components. To minimize this, capacitor types are selected on their linearity, and inductors are preferably realized without ferromagnetic materials. This is important for all filters (Tx and Rx).
   c) Nonlinearity of components in the high-current resonator. Here, it is especially important since it is in the high-current resonator where the highest currents and voltages occur. One key component to residual harmonic background is the non-linearity of the tuning capacitor assembly.
iv. Broadband noise generated by the drive-field amplifier. This is of particular interest according to the present invention, and explained above with reference to FIG. 6. Neither the Tx nor the Rx filter, both of which have a certain bandwidth, nor both in common, are able to suppress noise which is near around the fundamental frequency, e.g. +/−20 kHz, for a fundamental frequency of e.g. 150 kHz. In the spectrum, this sideband noise appears as symmetric shoulders around the suppressed fundamental frequency.

The disadvantage of known solutions is the enormous effort to implement it, e.g. by use of a large gradiometer, which is typically realized as a core-less toroidal inductor with more than 1 m of diameter. The Q-factor of the gradiometer coil needs to be very high, in order not to implement further losses, which generate noise. Therefore, a lot of special RF-Litz wire needs to be used, generating a lot of cost and weight. The present invention provides a light-weight alternative that is far easier to implement and does not lead to significant cost. It is able to alleviate at least limitations iii.a), iii.b) and iv).

FIGS. 7 to 14 show circuit diagrams of various embodiments of an MPI apparatus according to the present invention. Same elements as in the MPI apparatus 100 shown in FIG. 5 are provided with like reference numbers. However, not all elements shown in FIG. 5 are always shown in FIGS. 7 to 14.

Figure 7:
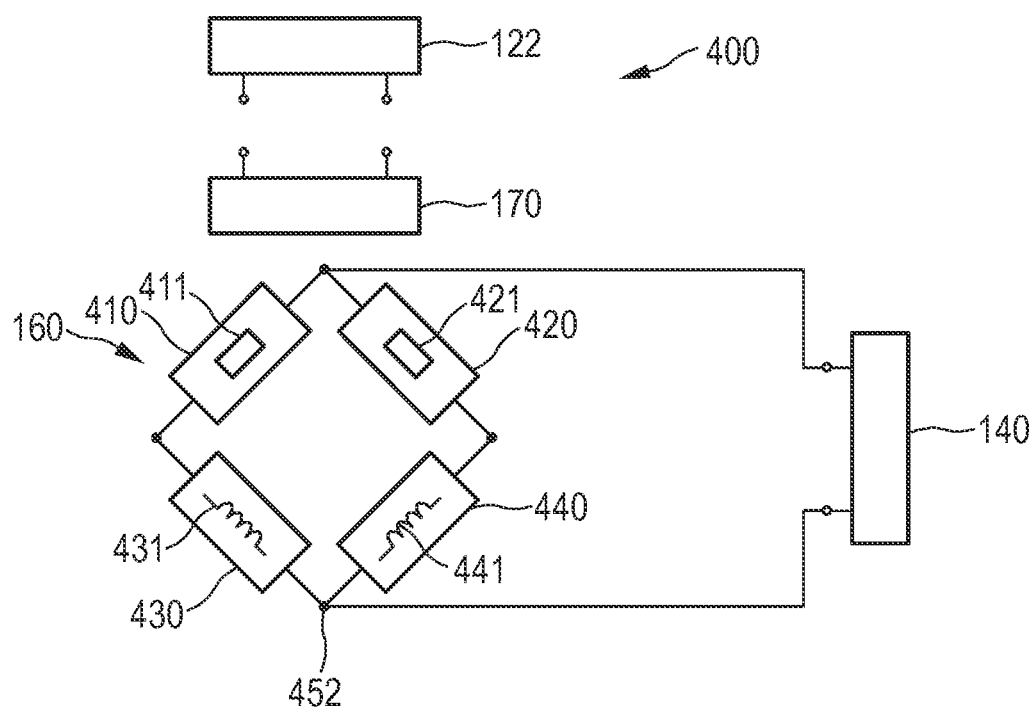
FIG. 7 shows a circuit diagram of a first, general embodiment of an MPI apparatus according to the present invention.

FIG. 7 shows a circuit diagram of a general layout of an MPI apparatus 400. The MPI apparatus 400 comprises the drive field signal generator unit 122, the signal receiving unit 140, the bridge unit 160 coupled between said drive field signal generator unit 122 and said signal receiving unit 140 and said coupling unit 170 coupled between the drive field signal generator unit 122 and the bridge unit 160 for coupling into the bridge unit 160. Said bridge unit 160 comprises four bridge sub-units 410, 420, 430, 440. A first bridge sub-unit 410 comprises a first inductive or capacitive coupling element 411. A second bridge sub-unit 420 comprises a second inductive or capacitive coupling element 421. A third bridge sub-unit 430, which is coupled in series with said first bridge sub-unit 410, comprises a measurement inductor 431. A fourth bridge sub-unit 440, which is coupled in series with said second bridge sub-unit 420, comprises said drive-receiving coil 441 (acting as joint transmit and receive coil). The signal receiving unit 140 is coupled to a first output terminal 451 arranged between the first and second bridge sub-units 410, 420 and a second output terminal 452 arranged between the third and fourth bridge sub-units 430, 440.

Figure 8:
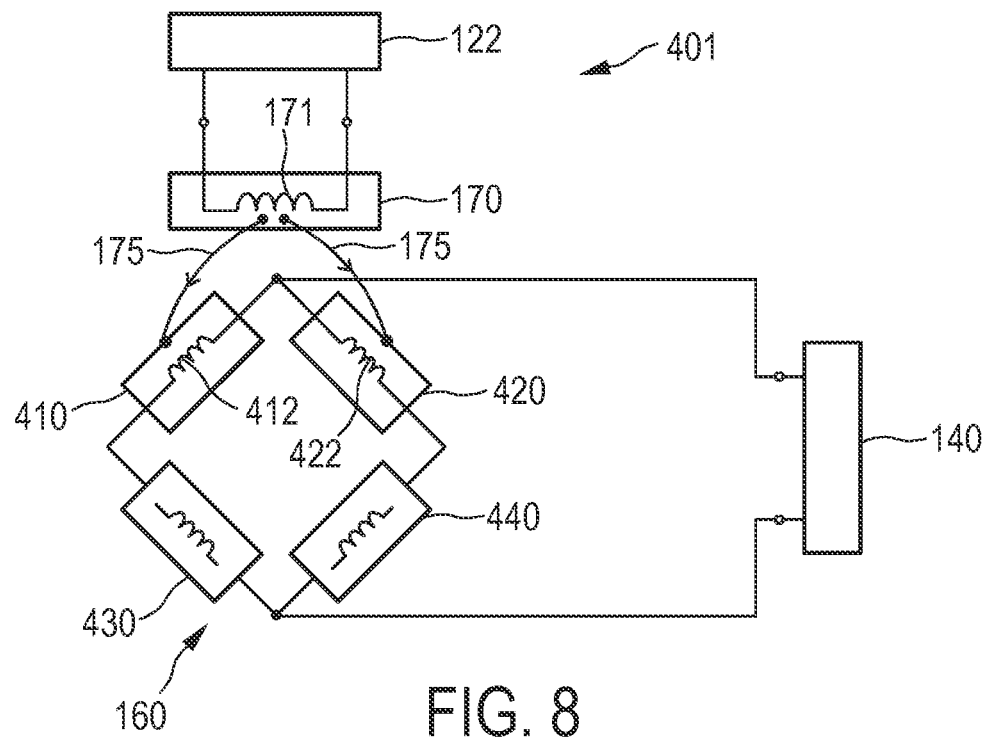
FIG. 8 shows a circuit diagram of a second embodiment of an MPI apparatus according to the present invention using inductive coupling.

FIG. 8 shows a circuit diagram of a second embodiment of an MPI apparatus 401 according to the present invention using inductive coupling. In this embodiment said coupling unit 170 is configured for inductive coupling and comprises a primary coupling inductor 171, wherein said first bridge sub-unit 410 comprises a first secondary coupling inductor 412 and said second bridge sub-unit 420 comprises a second secondary coupling inductor 422. Said primary coupling inductor 171 and said secondary coupling inductors 412, 422 are inductively coupled (indicated by arrows 175) like a transformer.

Figure 9:
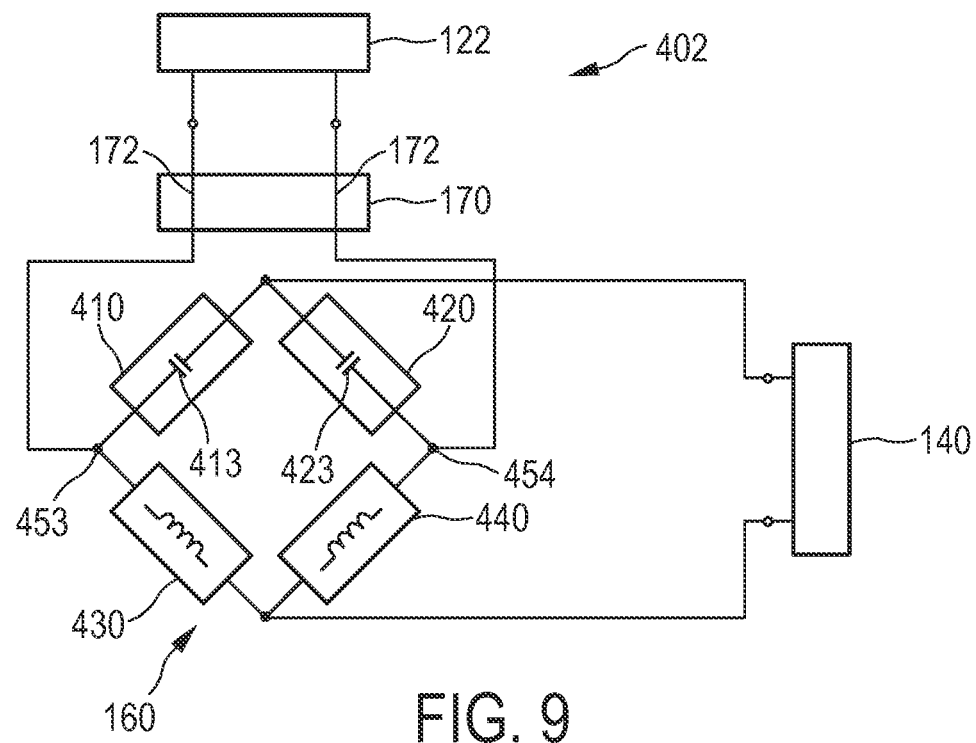
FIG. 9 shows a circuit diagram of a third embodiment of an MPI apparatus according to the present invention using capacitive coupling.

FIG. 9 shows a circuit diagram of a third embodiment of an MPI apparatus 402 according to the present invention using capacitive coupling. In this embodiment said coupling unit 170 is configured for capacitive coupling and comprises through-connections 172 for connecting said drive field signal generator unit 122 with a first input terminal 453 arranged between the first and third bridge sub-units 410, 430 and a second input terminal 454 arranged between the second and fourth bridge sub-units 420, 440. The first bridge sub-unit 410 comprises a first coupling capacitor 413, and the second bridge sub-unit 420 comprises a second coupling capacitor 423.

Independent of the present invention, the high-current resonator always has symmetry with respect to the output terminals where $U_{LNA}$ is measured, i.e. where the Low-Noise-Amplifier (preferably via an Rx filter, also called band stop filter) is connected. Not only the high-current resonator (i.e. the bridge unit 160), which basically is a loop with high-Q inductors and high-Q capacitors and a few resistive losses) as a whole, but each half (the right half of bridge sub-units 410, 430 and the left half of bridge sub-units 420, 440) of it are tuned to the resonance frequency, which is the respective drive-channel's frequency, also called fundamental frequency. This is done to cancel the fundamental frequency, which would otherwise be so strong, that it would saturate the LNA (and then it would become non-linear, which must be avoided). The cancellation, is however, limited to the fundamental frequency itself, not to other frequencies, i.e. it is not wideband.

The standard way of coupling the input signal (emanating originally from drive-field power amplifier, and then filtered by a Tx filter, also called pre-filter, or band pass filter) into the high-current resonator (i.e. the bridge unit 160) is to connect it to the primary side of an inductive coupling network (ICN). This, however, destroys symmetry, as it couples signals only into the left half (bridge sub-units 410, 430), and not into the right half (bridge sub-units 420, 440) of the resonator.

The present invention, instead, is based on a balanced bridge at the input towards the high-current resonator (ie. the bridge unit 160), as shown in FIGS. 7 to 9. Instead of coupling the input signal only to one coupling element, it is coupled symmetrically to two coupling elements 411 and 421 which are integrated symmetrically into the high-current resonator. So a signal is coupled both into the left (410, 430) and right (420, 440) half of the resonator, and the symmetry is kept.

FIGS. 10 to 13 shows more detailed circuit diagrams of embodiments of an MPI apparatus according to the present invention using inductive coupling, whereby the drive field signal generator unit 122 and the signal receiving unit 140 are not shown.

Figure 10:
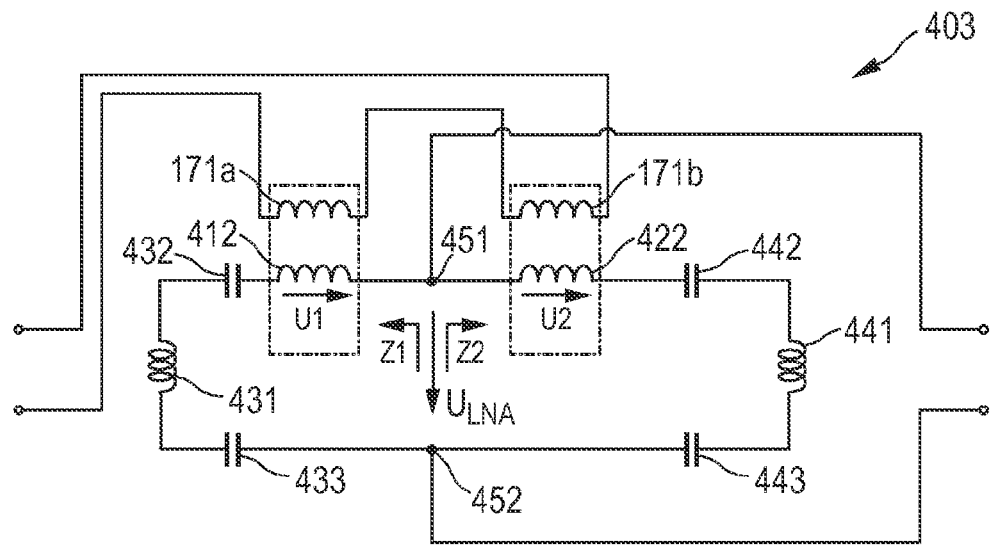
FIG. 10 shows a circuit diagram of a fourth embodiment of an MPI apparatus according to the present invention using inductive coupling.

The MPI apparatus 403 shown in FIG. 10 comprises an inductive coupling unit 170 having a first primary coupling inductor 171a and a second primary coupling inductor 171b, both being coupled in series, whereby it should be noted that a coupling in parallel will also work. The third and the fourth bridge sub-units 430, 440 each comprises two bridge capacitors 432, 433 and 442, 443 in series to said measurement inductor 431 and said drive-receiving coil 441, respectively. This embodiment provides a Tx symmetry (left/right) as well as an Rx symmetry (top/down).

The condition that shall be fulfilled to ensure that signal, at whatever frequency, so including the fundamental, noise, and harmonics, are suppressed on their way from the drive-field signal generator unit 122 towards the signal receiving unit 140 shall be explained with reference to FIG. 10. In particular, it shall be achieved that $U1/U2=Z1/Z2$, whereby U1 is the voltage induced into the first secondary coupling inductor 412, U2 is the voltage induced into the second secondary coupling inductor 422, Z1 is the inductance of the first and third bridge sub-units 410, 430 and Z2 is the inductance of the second and fourth bridge sub-units 420, 440. Hence, it is not required for the bridge to work that the loops are perfectly tuned to the fundamental frequency. But since this condition needs to be true at all frequencies, it implies that the resonance frequency can be the same. Further, it is not necessary for the left and right halves of the bridge unit to be identical. It is feasible to cope with a situation where Z1 and Z2 are unequal. In this case the coupling from the primary coupling inductor(s) 171 to the two secondary coupling inductors 412, 422 is preferably adapted.

For the measured voltage $U_{LNA}$ between the output terminals 451, 452 it holds: $U_{LNA}=U1-IZ1=U1-(U2+U2)/(Z1+Z2)*Z1=0$, which leads to the above mentioned condition that $U1/U2=Z1/Z2$. Ideally, the coupling by the coupling unit is fine-tuned and/or the components of the bridge unit (in particular the capacitors and/or the inductors) are selected such that $U1=U2$ and $Z1=Z2$.

In reality, it can be imagined to have the coupling unit 170 (i.e. the primary side) realized as a few flat windings (not distinguishing between two primary coupling inductors 171a, 171b) which can be moved geometrically, preferably around the geometrical symmetry axis of the two secondary windings (i.e. the secondary side) of the secondary coupling inductors 412, 422. Hence, by mechanically adjusting the position, it is possible to increase the induced voltage U1 and to reduce U2, thereby adapting to the required ratio Z1/Z2.

The effort to realize this is minimal. In fact, the primary side can be as simple as e.g. 5 windings of Litz-wire around a 0.2 m² area, without any cooling requirement. The secondary side is even simpler: it is not necessary to build a dedicated component. Instead, the area opened up between the other elements of the bridge unit suffices. Thus, basically one simple new component is brought into the vicinity of the existing high-current resonator to obtain already sufficient inductive coupling. Extra costs and cooling requirements are thereby avoided.

Figure 11:
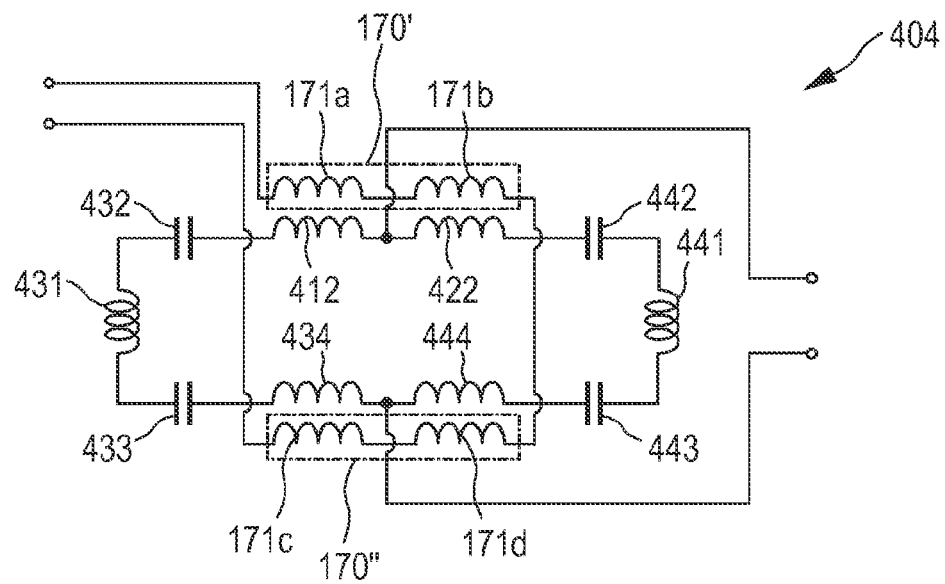
FIG. 11 shows a circuit diagram of a fifth embodiment of an MPI apparatus according to the present invention using inductive coupling.

The MPI apparatus 404 shown in FIG. 11 is very similar to the MPI apparatus 403, but the coupling unit comprises a first coupling sub-unit 170' (corresponding to the above shown coupling unit 170) and additionally comprises a second coupling sub-unit 170" comprising a third primary coupling inductor 171c and a fourth primary coupling inductor 171d, both being coupled in series. The four primary coupling inductors 171a-171d are coupled in series. Further, a third secondary coupling inductor 434 and a fourth secondary coupling inductor 444 are provided as part of the third and fourth bridge sub-units 430, 440 both coupled directly to the output terminal 452. This embodiment provides a Tx symmetry (left/right and top/down) as well as an Rx symmetry (top/down).

The embodiments of the MPI apparatuses described so far and as depicted in FIGS. 10 and 11 are electrically completely symmetric or "balanced" with respect to ground. In other embodiments described in the following and depicted in FIGS. 12 to 14 asymmetric or "unbalanced" realisations of the bridge unit are presented.

Figure 12:
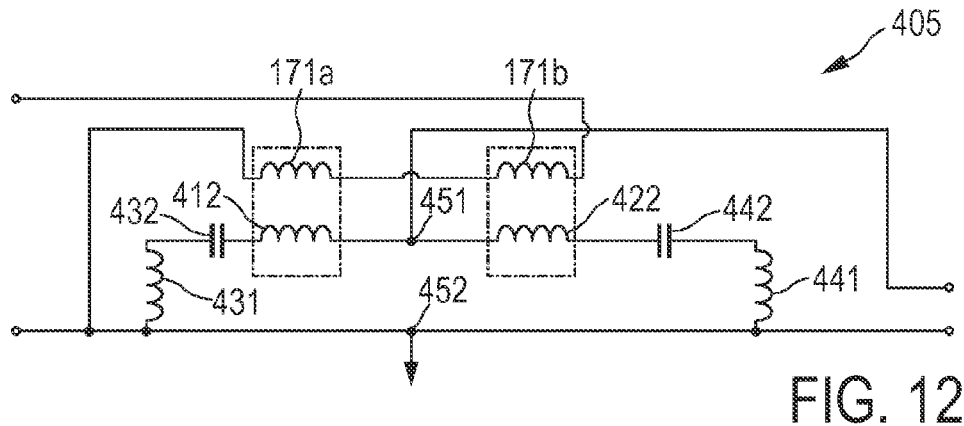
FIG. 12 shows a circuit diagram of a sixth embodiment of an MPI apparatus according to the present invention using inductive coupling.
Figure 13:
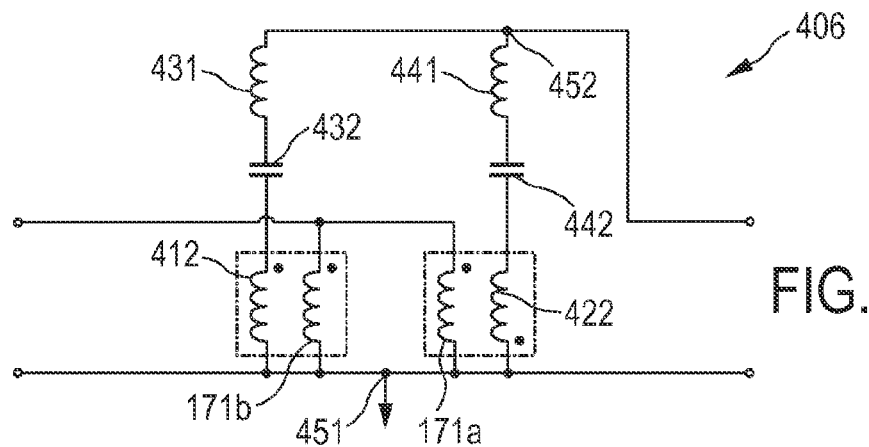
FIG. 13 shows a circuit diagram of a seventh embodiment of an MPI apparatus according to the present invention using inductive coupling.

The MPI apparatus 405 shown in FIG. 12 provides that the second output terminal 452 is coupled to ground, wherein the two primary coupling inductors 171a, 171b of the coupling unit are coupled in series. The MPI apparatus 406 shown in FIG. 13 provides that the first output terminal 451 is coupled to ground and that the two primary inductors 171a, 171b of the coupling unit coupled in parallel. The primary inductors 171a, 171b are preferably realized as one coil with opposed polarity compared to the respective secondary inductors 412, 422.

Figure 14:
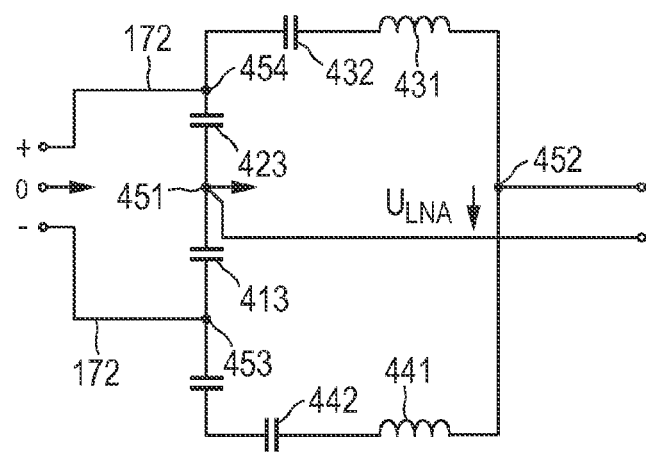
FIG. 14 shows a circuit diagram of an eighth embodiment of an MPI apparatus according to the present invention using capacitive coupling.

The MPI apparatus 407 shown in FIG. 14 uses capacitive coupling, i.e. the coupling unit here comprises through connections 172 to first and second input terminals 453, 454. Further, coupling capacitors 413, 423 are provided in the first and second bridge sub-units. This embodiment using capacitive coupling, and having a symmetric input to the bridge and an asymmetric output, can be further modified in the same or similar manner as shown above for the embodiments using inductive coupling.

In summary, the present invention provides a balanced bridge topology to suppress background harmonics by symmetry, which is less costly and less cumbersome than known solutions. The high-current resonator has now the symmetries of a balanced bridge, namely the input port/from amplifier has a left/right symmetry and the output port/towards LNA has a top/down symmetry. In contrast to known solutions the symmetries are orthogonal. The newly introduced coupling unit is an extra component, but as it has much less inductance it is not adding much size/volume/cost. Generally, both halves (right and left) of the bridge unit (i.e. the first and third bridge sub-units 410, 430 on the one hand and the second and fourth bridge sub-units 420, 440 on the other hand) are resonant to the drive-field frequency, thereby ensuring a wide-band (i.e. frequency-independent) isolation of the input port (from amplifier) to the output port (to LNA). This way, all signals emanating from the amplifier (fundamental, harmonics, spurious signals, noise) are isolated from the LNA.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:
1. An apparatus for influencing and/or detecting magnetic particles in a field of view, wherein the apparatus comprises:
   a selection field signal generator unit and selection field elements for generating a magnetic selection field having a pattern in space of its magnetic field strength such that a first sub-zone having a low magnetic field strength where a magnetization of the magnetic particles is not saturated and a second sub-zone having a higher magnetic field strength where the magnetization of the magnetic particles is saturated are formed in the field of view,
   a drive field signal generator unit, a signal receiving unit and a drive-receiving coil, said drive-receiving coil being configured both for changing a position in space of the first and second sub-zones in the field of view by a magnetic drive field so that the magnetization of the magnetic particles changes locally and for acquiring detection signals, wherein the detection signals depend on the magnetization of the magnetic particles in the field of view, wherein the magnetization is influenced by the change in the position in space of the first and second sub-zones,
   a bridge unit coupled between said drive field signal generator unit and said signal receiving unit, said bridge unit comprising
      a first bridge sub-unit comprising a first inductive or capacitive coupling element,
      a second bridge sub-unit comprising a second inductive or capacitive coupling element,
      a third bridge sub-unit coupled in series with said first bridge sub-unit, said third bridge sub-unit comprising a measurement inductor, and
      a fourth bridge sub-unit coupled in series with said second bridge sub-unit, said fourth bridge sub-unit comprising said drive-receiving coil, and
      a coupling unit coupled between the drive field signal generator unit and the bridge unit for coupling into the bridge unit,
   wherein the signal receiving unit is coupled to a first output terminal arranged between the first and second bridge sub-units and a second output terminal arranged between the third and fourth bridge sub-units.

2. The apparatus as claimed in claim 1,
wherein said coupling unit is configured for inductive coupling and comprises a primary coupling inductor, wherein said first bridge sub-unit comprises a first secondary coupling inductor and said second bridge sub-unit comprises a second secondary coupling inductor.

3. The apparatus as claimed in claim 1,
wherein said coupling unit is configured for capacitive coupling and comprises through-connections for connecting said drive field signal generator unit with a first input terminal arranged between the first and third bridge sub-units and a second input terminal arranged between the second and fourth bridge sub-units.

4. The apparatus as claimed in claim 1,
wherein the coupling unit and/or the bridge unit are configured to obtain that U1/U2=Z1/Z2, wherein U1 is a voltage induced into the first inductive or capacitive coupling element, U2 is a voltage induced into the second inductive or capacitive coupling element, Z1 is a impedance of the series connection of the first and third bridge sub-units and Z2 is an impedance of the series connection of the second and fourth bridge sub-units.

5. The apparatus as claimed in claim 4,
wherein the coupling unit and/or the bridge unit are configured to obtain that U1=U2 and Z1=Z2.

6. The apparatus as claimed in claim 4,
wherein the value of the first inductive or capacitive coupling element and/or the second inductive or capacitive coupling element are selected to obtain that U1/U2=Z1/Z2.

7. The apparatus as claimed in claim 2,
wherein coupling unit is configured to mechanically change or set a coupling rate of the primary coupling inductor with the first and/or the second coupling inductor.

8. The apparatus as claimed in claim 1,
wherein said third and/or fourth bridge sub-unit comprises one or more bridge capacitors in series to said measurement inductor and said drive-receiving coil, respectively.

9. The apparatus as claimed in claim 2,
wherein said third bridge sub-unit comprises a third secondary coupling inductor coupled in series to said measurement inductor, said fourth bridge sub-unit comprises a fourth secondary coupling inductor coupled in series to said drive-receiving coil, and said coupling unit comprises a first coupling sub-unit for coupling with said first and second secondary coupling inductors and a second coupling sub-unit for coupling with said third and fourth secondary coupling inductors.

10. The apparatus as claimed in claim 2,
wherein the primary coupling inductor comprises two primary coupling inductors for separately coupling to the first and second secondary coupling inductors, wherein said two primary coupling inductors are coupled in series or in parallel.

11. The apparatus as claimed in claim 3,
wherein said first bridge sub-unit comprises a capacitor and said second bridge sub-unit comprises a capacitor.

12. The apparatus as claimed in claim 1,
wherein the series connection of the first and third bridge sub-units and/or the series connection of the second and fourth bridge sub-units are configured to be in resonance with a drive field frequency of the magnetic drive field.

13. The apparatus as claimed in claim 4,
wherein the value of the first inductive or capacitive coupling element and/or the second inductive or capacitive coupling element are selected to obtain that U1=U2 and Z1=Z2.

14. A method for influencing and/or detecting magnetic particles in a field of view, wherein the method comprises the acts of:
generating a magnetic selection field having a pattern in space of its magnetic field strength such that a first sub-zone having a low magnetic field strength where a magnetization of the magnetic particles is not saturated and a second sub-zone having a higher magnetic field strength where the magnetization of the magnetic particles is saturated are formed in the field of view,
changing a position in space of the first and second sub-zones in the field of view by a magnetic drive field generated by a drive field signal generator unit so that the magnetization of the magnetic particles changes locally by one or more drive-receiving coils,
acquiring detection signals by the one or more drive-receiving coils, wherein the detection signals depend on the magnetization of the magnetic particles in the field of view, wherein the magnetization is influenced by the change in the position in space of the first and second sub-zones,
coupling energy into a bridge unit coupled between said drive field signal generator unit and a signal receiving unit, said bridge unit comprising
  a first bridge sub-unit comprising a first inductive or capacitive coupling element,
  a second bridge sub-unit comprising a second inductive or capacitive coupling element,
  a third bridge sub-unit coupled in series with said first bridge sub-unit, said third bridge sub-unit comprising a measurement inductor, and
  a fourth bridge sub-unit coupled in series with said second bridge sub-unit, said fourth bridge sub-unit comprising said one or more drive-receiving coils, and
obtaining the detection signals by the signal receiving unit coupled to a first output terminal arranged between the first and second bridge sub-units and a second output terminal arranged between the third and fourth bridge sub-units.

15. A computer comprising a processor for influencing and/or detecting magnetic particles in a field of view, wherein the processor is configured to perform the acts of:
causing generation of a magnetic selection field having a pattern in space of its magnetic field strength such that a first sub-zone having a low magnetic field strength where a magnetization of the magnetic particles is not saturated and a second sub-zone having a higher magnetic field strength where the magnetization of the magnetic particles is saturated are formed in the field of view,
causing a change in a position in space of the first and second sub-zones in the field of view by a magnetic drive field generated by a drive field signal generator unit so that the magnetization of the magnetic particles changes locally by one or more drive-receiving coils,
causing acquisition of detection signals by the one or more drive-receiving coils, wherein the detection signals depend on the magnetization of the magnetic particles in the field of view, wherein the magnetization is influenced by the change in the position in space of the first and second sub-zones,
causing coupling of energy into a bridge unit coupled between said drive field signal generator unit and a signal receiving unit, said bridge unit comprising a first bridge sub-unit comprising a first inductive or capacitive coupling element, a second bridge sub-unit comprising a second inductive or capacitive coupling element, a third bridge sub-unit coupled in series with said first bridge sub-unit, said third bridge sub-unit comprising a measurement inductor, and a fourth bridge sub-unit coupled in series with said second bridge sub-unit, said fourth bridge sub-unit comprising said one or more drive-receiving coils, and causing obtaining the detection signals by the signal receiving unit coupled to a first output terminal arranged between the first and second bridge sub-units and a second output terminal arranged between the third and fourth bridge sub-units.

* * * * *